United States Patent

Ehara et al.

Patent Number: 5,131,912
Date of Patent: Jul. 21, 1992

[54] 2-PART HAIR DYEING AGENT

[75] Inventors: Masashi Ehara, Osaka; Akio Fukumashi, Ohtsu, both of Japan

[73] Assignee: Sunstar Kabushiki Kaisha, Osaka, Japan

[21] Appl. No.: 618,230

[22] Filed: Nov. 21, 1990

[30] Foreign Application Priority Data

Nov. 30, 1989 [JP] Japan .................................. 1-311443

[51] Int. Cl.$^5$ .............................................. A61K 7/13
[52] U.S. Cl. ............................................ 8/405; 8/406; 8/408; 8/409; 8/410; 8/421
[58] Field of Search ................... 8/405, 406, 421, 408, 8/409, 410

[56] References Cited

U.S. PATENT DOCUMENTS

| 3,861,868 | 1/1975 | Milbrada ................................. 8/410 |
| 3,975,515 | 8/1976 | Wajaroff et al. ........................ 8/412 |
| 4,529,404 | 7/1985 | Feinland et al. ........................ 8/410 |
| 4,656,030 | 4/1987 | Sebag et al. ............................. 8/405 |
| 4,797,130 | 1/1989 | Clausen et al. ......................... 8/409 |

FOREIGN PATENT DOCUMENTS 48-85745 of 1973 Japan .
63-174917 7/1988 Japan .
1-18048 4/1989 Japan .

OTHER PUBLICATIONS

English Abstract of JP Appln. No. 62-5836/1987 (Laid-Open No. 174917/1988).
English Abstract of JP Appln. No. 59-203389/1984 (Published No. 1-18048/1989).
English Abstract of JP Appln. No. 63-174917.

Primary Examiner—A. Lionel Clingman
Assistant Examiner—William S. Parks
Attorney, Agent, or Firm—Birch, Stewart, Kolasch & Birch

[57] ABSTRACT

Novel durable 2-part hair dyeing agents composed of a first agent comprising as essential components at least one compound that forms $HCO_3-$ by dissociation in water, an alkali generating substantially no irritating odor and a dye for hair and having a pH of 8.2 to 9.0. and a second agent comprising as essential components hydrogen peroxide and a buffer solution and having a pH of 2.0 to 4.0, the weight ratio of the first agent and the second agent to be mixed being such that the pH of the mixture of the two is in a range of from 6.5 to 7.9. These 2-part hair dyeing agents require only a short dyeing time, create little damage to hair and no irritating or disagreeable odor and have high dyeing effect.

5 Claims, 2 Drawing Sheets

2-PART HAIR DYEING AGENT

BACKGROUND OF THE INVENTION

1. Field of the invention

The present invention relates to a 2-part hair dyeing agent, and more specifically to a 2-part durable hair dyeing agent emanating no irritating odor, causing little damage to hair and requiring comparatively short time for the dyeing.

2. Description of the prior art

Hair dyeing agents are classified into two large groups: durable hair dyeing agents which do not decolor by shampooing, and temporary hair dyeing agents which decolor by shampooing, the former being more widely used at present.

Conventional durable hair dyeing agents contain as essential components a first agent comprising an alkali and a hair dye such as an oxidation dye or direct dye and a second agent comprising hydrogen peroxide.

The first and second agents are mixed with each other just before use and then applied to hair. The dye molecules penetrate into hair, and nascent oxygen generating from hydrogen peroxide decolors (bleaches) hair. Where an oxidation dye is used, the nascent oxygen also oxidizes and polymerizes the oxidation dye to develop color. The alkali contained in the first agent swells hair, thereby facilitating the penetration of dye molecules into hair, and at the same time promotes generation of nascent oxygen from hydrogen peroxide, thereby increasing the effect of dyeing. Ammonia, mono-, di- and trialkanolamine and the like are generally used as the alkali.

However, while these alkalis used increase the dyeing effect, the following problems associated with their use have been pointed out.

(1) The pH of the first agent is generally so adjusted that the 2-part hair dyeing agent obtained by mixing the first and second agents will be in the range of from 9 to 11. In this pH range, however, free alkali is present in a large amount, which irritates skin and causes hair to be damaged.

(2) Where ammonia, which is volatile, is used as alkali, its irritating odor is disagreeable.

Where mono-, di- or triethanol amine is used, which is only a little volatile and hence not so disagreeable, the alkali remains inside hair after the use and attacks keratin in hair, thereby causing the hair to be damaged.

Japanese Patent Application Laid-open No. 85745/1973 discloses a 2-part hair dyeing agent utilizing as alkali an ammonium salt and a base instead of aqueous ammonia, which is said to be successful in suppressing the above hair damage and irritating or disagreeable odor.

The 2-part hair drying agent according to the invention described in the above application comprises, for example, a first agent consisting of a hair dye and a base such as sodium hydroxide and a second agent consisting of urea hydrogen peroxide as an oxidizing agent and an ammonium salt such as ammonium chloride.

This hair dyeing agent, when used after mixing is said to emanate no irritating odor since the ammonium salt and the base gradually generate ammonia in a minimum amount required, thus being different from the usual cases where aqueous ammonia is directly incorporated in a first agent.

However, this 2-part hair dyeing agent comprising an ammonium salt and a base as alkali must generate ammonia in bleaching (decoloring) and dyeing, and hence does not differ from conventional 2-part dyeing agents, in that ammonia is still being used for bleaching and dyeing. The use of this agent therefore cannot fully eliminate disagreeable odor, but simply reduce it to a certain degree.

Furthermore, this agent creates another problem, namely, the problem of requiring a considerably long time of about 40 minutes, since ammonia generates only gradually, as shown in the above application.

As a result of an intensive study, the present inventors have found that the above problems can all be solved by providing a first agent comprising a specific compound capable of promoting generation of nascent oxygen and a hair dye and a second agent comprising hydrogen peroxide, and further incorporating an alkali that generates substantially no irritating odor into the first agent and incorporating a buffer solution to stabilize the hydrogen peroxide in the second agent, both agents being prepared in such amounts as to permit the pH to be in a nearly neutral zone, after the mixing of the two agents. The present invention was completed based on this finding.

SUMMARY OF THE INVENTION

Accordingly, an object of the present invention is to provide a 2-part hair dyeing agent that requires only a short dyeing time, creates little damage to hair and no irritating or disagreeable odor after dyeing, thus rendering dyeing operation acceptable, and has high dyeing effect.

For the purpose of achieving this object, the present invention provides a 2-part hair dyeing agent composed of a first agent comprising as essential components at least one compound that forms $HCO_3^-$ by dissociation in water, an alkali generating substantially no irritating odor and a dye for hair and having a pH of 8.2 to 9.0, and a second agent comprising as essential components hydrogen peroxide and a buffer solution and having a pH of 2.0 to 4.0, the weight ratio of the first agent and the second agent to be mixed being such that the pH of the mixture of the two is within a range of from 6.5 to 7.9.

BRIEF DESCRIPTION OF THE DRAWINGS

A more complete appreciation of the invention and many of the attendant advantages thereof will be readily obtained as the same become better understoods by reference to the following detailed description when considered in connection with the accompanying drawings, wherein.

DESCRIPTION OF THE PREFERRED EMBODIMENTS

Figure 1:
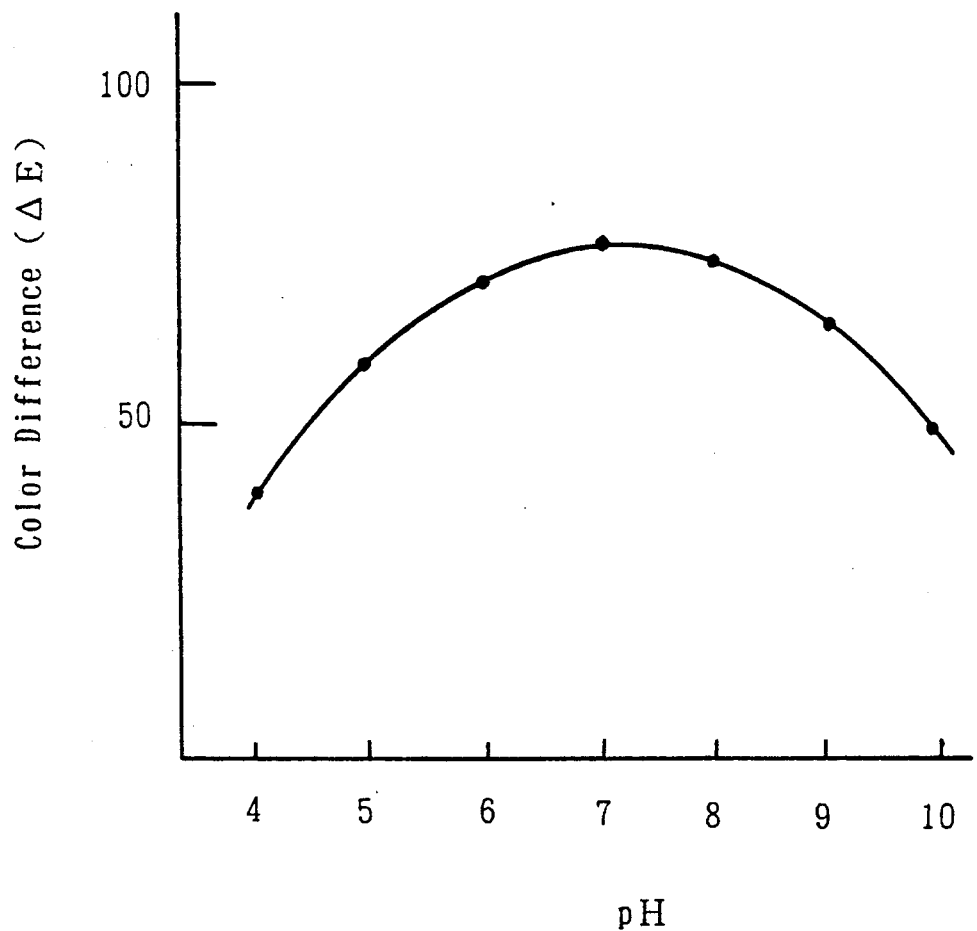
FIG. 1 shows the relationship between the dyeing force and pH of a hair dyeing agent.

In the hair dyeing agent of present invention, the first agent comprises as essential components at least one compound that forms $HCO_3^-$ by dissociation in water, an alkali generating substantially no irritating odor and a dye for hair and having a pH of 8.2 to 9.0.

Examples of the compound that forms $HCO_3^-$ by dissociation in water (hereinafter referred to as "ion-forming compound") are $Na_2CO_3$, $NaHCO_3$, $K_2CO_3$, $KHCO_3$, $(NH_4)_2CO_3$, $NH_4HCO_3$, $CaCO_3$ and Ca(H-

$CO_3)_2$. These compounds may be used singly or, as required, in combination.

Any alkali generating substantially no irritating odor can be used and its examples are hydroxides of alkali metals, such as sodium hydroxide and potassium hydroxide, hydroxides of alkali earth metals, such as calcium hydroxide and magnesium hydroxide, basic amino acids such as L-arginine, lysine, oxylysine and histidine, and aminoalkylpropanediol.

Known hair dyes can be used as the dye for hair in the present invention and they include intermediates of oxydation dyes, couplers, direct dyes and other conventional hair dyes.

Examples of the above hair dyes are 5-amino-o-cresol, 2-amino-4-nitrophenol, 2-amino-5-nitrophenol, 1-amino-4-methylaminoanthraquinone, 3,3'-iminodiphenol, 2,4-diaminophenol hydrochloride, toluene-2,5-diamine hydrochloride, nitro-p-phenylenediamine hydrochloride, p-phenylenediamine hydrochloride, N-phenyl-p-phenylenediamine hydrochloride, m-phenylenediamine hydrochloride, o-aminophenol, catechol, resorcinol, N-phenyl-p-phenylenediamine acetate, 1,4-diaminoanthraquinone, 2,6-diaminopyridine, 1,5-dihydroxynaphthalene, diphenylamine, toluene-2,5-diamine, toluene-3,4-diamine, α-naphthol, nitro-p-phenylenediamine, p-aminophenylsulfamic acid, p-aminophenol, p-nitro-o-phenylenediamine, p-phenylenediamine, p-methylaminophenol, picramic acid, sodium picramate, picric acid, N,N'-bis(4-aminophenyl)-2,5-diamino-1,4-quinonediimine, sodium 2-hydroxy-5-nitro-2'4'diaminoazobenzene-5-sulfonate, hydroquinone, pyrogallol, N-phenyl-p-phenylenediamine, phloroglucinol, haematin, gallic acid, m-aminophenol, m-phenylenediamine, 5-amino-o-cresol sulfate, 2-amino-5-nitrophenol sulfate, o-aminophenol sulfate, o-chloro-p-phenylenediamine sulfate, 4,4'-diaminodiphenylamine sulfate, toluene-2,5-diamine sulfate, nitro-p-phenylenediamine sulfate, p-aminophenol sulfate, p-nitro-o-phenylenediamine sulfate, p-nitro-m-phenylenediamine sulfate, p-phenylenediamine sulfate, p-methylaminophenol sulfate, m-aminophenol sulfate, m-phenylenediamine sulfate, 2,4-diaminophenoxyethanol hydrochloride and 5-(2-hydroxyethylamino)-2-methylphenol.

These dyes may be used singly or, as required, in combination.

The ion-forming compound is incorporated in the first agent in an amount of 0.1 to 30% by weight (hereinafter "% by weight" is simply indicated by "%") based on the total weight of the first agent, preferably 1 to 20% on the same basis, from the viewpoint of the incorporation effect.

The hair dye is incorporated, depending on the type, in a similar amount to the amounts with conventional hair dyes and generally in an amount of 0.001 to 10% based on the total weight of the first agent.

The alkali is incorporated in such an amount that the pH of the first agent will be 8.2 to 9.0. The alkali acts as a pH adjusting agent in view of the fact that the above ion-forming compound is unstable in the pH range of less than 8.2.

The second agent of the present invention comprises as essential components hydrogen peroxide and a buffer solution.

Hydrogen peroxide is, for the purpose of enhancing dyeing effect, incorporated generally in an amount of 0.1 to 6% based on the total weight of the second agent, preferably 1 to 6% on the same basis.

The buffer solution is incorporated to stabilize hydrogen peroxide. Since hydrogen peroxide is stable in the pH range from 2.0 to 4.0, it is necessary to use a buffer solution having a pH value within this range.

Examples of the buffer solution are aqueous solutions of sodium dihydrogenphosphate/phosphoric acid, disodium hydrogenphosphate/phosphoric acid, potassium chloride/hydrochloric acid, potassium hydrogenphthalate/hydrochloric acid, sodium citrate/hydrochloric acid, potassium dihydrogencitrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid, and other buffer solutions can also be used.

In the hair dyeing agent of the present invention, the mixing ratio of the first agent and the second agent is so selected that the resulting mixture will have a pH of 6.5 to 7.9, since the dyeing effect exhibits the highest dyeing effect in this pH range. Accordingly, the pH of the solution obtained by mixing the 2-part hair dyeing agent of the present invention is lower than that of conventional hair dyeing agent incorporating aqueous ammonia, i.e., 9.0 to 11.0, whereby the hair treated swells only to a small extent and suffers no damage and also the irritation to skin is relieved.

Although it is undeniable that the hair thus swollen to a small extent by an alkali having such a low pH will allow dye particles to penetrate not so fully into individual hairs, this fact causes no problem in practice because the resulting dye penetration still assures good dyeing effect.

In the present invention, the molar ratio of the ion-forming compound in the first agent and hydrogen peroxide in the second agent is preferably in a range of 1/20 to 20/1, more preferably in a range of 1/5 to 5/1. If the ratio is not within this range, the bleaching effect will be small, whereby only a similar dyeing effect to that of conventional hair dyeing agents utilizing solely hydrogen peroxide.

The hair dyeing agents of the present invention can be prepared according to desired prescriptions in the usual manner, into various forms such as shampoo, "treatment" liquid and "pretreatment" liquid. For example, there can be prepared a first agent of powder form and a second agent of aqueous solution; a first agent of nonaqueous gel and a second agent of aqueous solution; and other combinations. There may also be prepared other forms such as milky lotion, cream and paste, by adding various ingredients.

There are no restrictions with respect to usable ingredients other than the essential components, and, for instance, either one or both of the first agent and the second agent of the 2-part hair dyeing agent can incorporate a hair conditioning agent to improve comb-ability of the dyed hair after being shampooed.

Examples of the hair conditioning agent now available are SM-702C (amino-modified silicone, made by Toray Silicone Co.), CATIOL HC-100 (cationized cellulose, made by Toho Chemical Industry Co.), PEPTIDE PA-10 (hydrolyzed polypeptide; solid content: 100%, $\overline{Mn}$: about 1,000; made by Nippi Inc.), PROMOIS W-32R (hydrolyzed polypeptide; solid content: 30%, $\overline{Mn}$: about 400; made by Seiwa Kasei Co., Ltd.), PROMOIS W-52QP (hydrolyzed polypeptide; solid content: 90%, $\overline{Mn}$: about 2,000; made by Seiwa Kasei Co., Ltd.), PROMOIS WK-HQ (hydrolyzed polypeptide; solid content: 25%, $\overline{M}n$: about 1,000; made by Seiwa Kasei Co., Ltd.) and CROTEIN Q (hydrolyzed polypeptide; solid content: 90%, $\overline{M}n$: about 12,500; made by Croda Japan K.K.).

Other various solubilizing agents, emulsifiers, solvents, wetting agents, sequestering agents, foaming agents, foaming assistants, oils, wax, hydrocarbons, aliphatic acids, alcohols, polyhydric alcohols, ester oils, perfumes and the like may also be incorporated singly or in an appropriate combination.

The 2-part hair dyeing agents of the present invention can be used in the same manner as conventional 2-part hair dyeing agents. For instance, the two constituting agents are mixed in a prescribed ratio and immediately thereafter the mixture is applied uniformly to hair. The hair is then rinsed with warm water, shampooed and dried.

Other features of the invention will become apparent in the course of the following descriptions of exemplary embodiments which are given for illustration of the invention and are not intended to be limiting thereof.

EXAMPLES

(I) Hair dyeing tests

Hair dyeing agents, A through G, of compositions and having different pH's as shown in Table 1 were prepared. Using these hair dyeing agents just after preparation, the relationship between the hair dyeing property and the pH was studied in the following manner. In Table 1, "%" means "% by weight".

Each hair dyeing agent was, in an amount of 0.2 g, applied to 2 g of an untreated blond hair, and the hair was then allowed to stand at 25° C. for 20 minutes, to complete hair dyeing. After the dyeing, the hairs were rinsed with a water stream at 40° C. and air-dried. The color differences, ($\Delta E$), between the dyed hairs and the pH of the corresponding hair dyeing agents were measured with a high-speed spectrocalorimeter (CMS-1,200, made by Murakami Color Research Laboratory). Here a larger color difference shows a higher dyeing property of the hair dyeing agent tested.

FIG. 1 shows a graph with the coordinate representing the color difference ($\Delta E$) and the abscissa the pH. In the FIGURE, the values of $\Delta E$ corresponding to the pH's of 4, 5, 6, 7, 8, 9 and 10 are 39.8, 58.3, 72.6, 78.0, 74.6, 67.2 and 57.1, respectively. It is apparent from the FIGURE that the hair dyeing agents having a pH of 6.5 to 7.9 according to the present invention have excellent hair dyeing property.

TABLE 1

|  | A | B | C | D | E | F | G |
|---|---|---|---|---|---|---|---|
| Components of 1st agent | | | | | | | |
| p-Phenylenediamine | 0.3 | same as left | same as left | same as left | same as left | same as left | same as left |
| Catechol | 0.3 | | | | | | |
| Disodium edetate | 0.2 | | | | | | |
| Sodium sulfite | 0.8 | | | | | | |
| Propylene glycol | 10.0 | | | | | | |
| Ammonium hydrogencarbonate | 8.0 | | | | | | |
| 0.1N—KOH | 0.1 | 0.1 | 0.1 | 0.1 | to pH = 8* | — | — |
| 1N—KOH | — | — | — | — | — | to pH = 9 | to pH = 10 |
| Purified water | 20.0 | 20.0 | 20.0 | 20.0 | 20.0 | 20.0 | 20.0 |
| Components of 2nd agent | | | | | | | |
| Sodium hydrogenephosphate | 0.1 | 0.1 | 0.1 | 0.1 | 0.1 | 0.1 | 0.1 |
| Phosphoric acid | to pH = 4 | to pH = 5 | to pH = 6 | to pH = 7 | 0.1 | 0.1 | 0.1 |
| Aqueous hydrogen peroxide (35%) | 15.0 | 15.0 | 15.0 | 15.0 | 15.0 | 15.0 | 15.0 |
| Purified water | balance | balance | balance | balance | balance | balance | balance |
| pH | 4.0 | 5.0 | 6.0 | 7.0 | 8.0 | 9.0 | 10.0 |

*"to pH = 8" means that the reagent is added in such an amount as to adjust the pH of the resulting mixture to 8.

(II) Hair damage tests

Hairs were dyed with hair dyeing agents H and I having compositions as shown in Table 2 and tested for the degree of damage, in the following manner. In Table 1, "%" means "% by weight".

The hair dyeing agents were prepared by mixing 0.1 g each of the corresponding first agent and second agent. Hairs (Japanese chemically untreated hair) were each dyed in the same manner as in the above (I) with 0.2 g each of the thus prepared hair dyeing agent. Then, 30 pieces of hairs each of the thus dyed hairs were immersed in water. The wet strengths of the specimen hairs were determined using a tensile tester (TENTION/UTM-II-20, made by Toyo Baldwin Co.). The load in newton (N) required for extending the specimen tested by 20% is taken as a measure of the tensile strength and named "20% INDEX".

Figure 2:
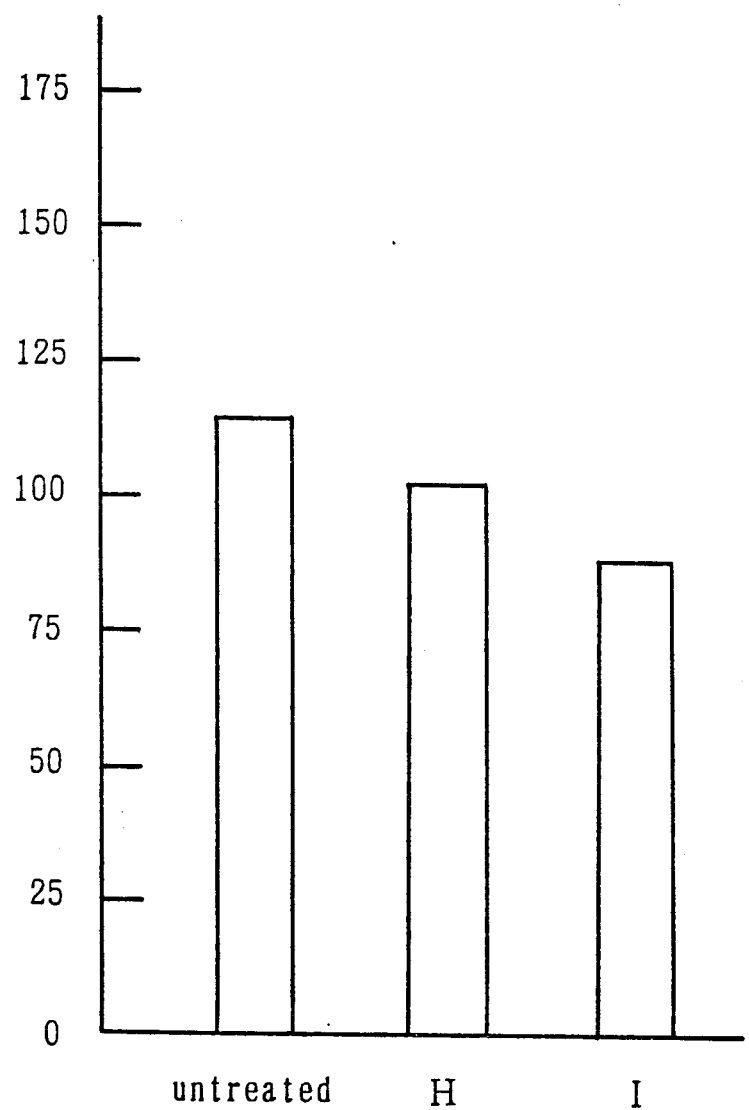
FIG. 2 shows to what extent hair is damaged by dyeing.

FIG. 2 is a bar graph showing the results of the above tests, where the coordinate represents the average of "20% INDEX/cross-sectional area of a hair" values {quotinent ($N/m^2$) obtained by dividing the load (N) at 20% elongation by the cross-sectional area ($m^2$) of the specimen hair filament tested} and the abscissa represents the types of hair tested. The graph also includes the undyed hair as control.

As apparent from the FIGURE, the hair dyed with the hair dyeing agent H of the present invention has a (20% INDEX/cross-sectional area) value of $103.2 \pm 21.1$ ($\times 10^6$ $N/m^2$), which has no significant difference from that of the hair before being dyed, $117.4 \pm 21.2$ ($\times 10^6$ $N/m^2$). This means that the dyed hair showed no significant decrease in the tensile strength.

On the other hand, the hair dyed with a conventional hair dyeing agent I showed $90.4 \pm 23.6$ ($\times 10^6$ $N/m^2$), a noticeable drop in the tensile strength, proving that the hair had been damaged.

TABLE 2

|  | H | I |
|---|---|---|
| Composition of 1st agent | | |
| Ammonium hydrogencarbonate | 4.0 | — |
| Oleic acid | 10.0 | 10.0 |
| 50% ethyl alcohol | 12.0 | 12.0 |
| Propylene glycol | 8.0 | 8.0 |
| Disodium edetate | 0.3 | 0.3 |

TABLE 2-continued

|  | H | I |
|---|---|---|
| Polyoxyethylene (10) oleyl ether | 6.0 | 6.0 |
| Polyoxyethylene (2) oleyl ether | 4.0 | 4.0 |
| p-Phenylenediamine | 1.0 | 1.0 |
| o-Aminophenol | 0.2 | 0.2 |
| m-Aminophenol | 0.2 | 0.2 |
| Aqueous ammonia | — | to pH = 9 |
| 5N—NaOH | 2.0 | — |
| Purified water | balance | balance |
| Composition of 2nd agent |  |  |
| Aqueous hydrogen peroxide | 14.0 | 14.0 |
| Phosphoric acid | 1.0 | 0.1 |
| Disodium hydrogenphosphate | 1.0 | — |
| Purified water | balance | balance |

(III) Smell test

The hair dyeing agents H and I used in the above (II), each weighing 10 g, were tested for the presence of any irritating odor through the sense of smell by 35 panelists picked randomly.

The results are shown in Table 3, where:

TABLE 3

| Evaluation | ◯ | △ | X | XX |
|---|---|---|---|---|
| H | 35 | 0 | 0 | 0 |
| I | 0 | 5 | 13 | 17 |

◯ indicates "no irritating odor",
△ "weak irritating odor",
X "ordinary irritating odor" and
XX "strong irritating odor.
Note: Figures in the table show the numbers of the panelists.

As apparent from the table, all the panelists did not feel any irritating odor at all with the hair dyeing agent H of the present invention, while with I, the conventional hair dyeing agent tested, none of these felt irritating odor and as many as 17 panelists felt strong irritating odor, which should cause a problem in practical use.

Obviously, numerous modifications and variations of the present invention are possible in light of the above teaching. It is therefore to be understood that within the scope of the appended claims, the invention may be practiced otherwise than as specifically described herein.

What is claimed is:

1. A 2-part hair dyeing agent which comprises:
a first agent comprising at least one compound capable of forming $HCO_3-$ by dissociation in water, a hair dye, and an alkali which generates substantially no irritating odor selected from the group consisting of an alkali metal hydroxide, an alkali earth metal hydroxide, lysine, oxylysine, histidine and aminoalkylpropanediol and in an amount such that the pH of the first agent is in the range of from 8.2 to 9.0, and
a second agent comprising hydrogen peroxide and a buffer solution in an amount such that the pH of the second agent is in the range of from 2.0 to 4,0,
wherein the weight ratio of the first agent to the second agent when mixed, is characterized in that the resulting pH of the mixture is within a range of from 6.5 to 7.9.

2. The 2-part hair dyeing agent according to Claim 1, wherein said compound is selected from the group consisting of $NaHCO_3$, $NH_4HCO_3$, $KHCO_3$, $Ca(HCO_3)_2$, $Na_2CO_3$, $(NH_4)_2CO_3$, $K_2CO_3$ and $CaCO_3$.

3. The 2-part hair dyeing agent according to claim 1, wherein said buffer solution is an aqueous solution of sodium dihydrogenphosphate/phosphoric acid, disodium hydrogenphosphate/phosphoric acid, potassium chloride/hydrochloric acid, potassium hydrogenphthalate/hydrochloric acid, sodium citrate/hydrochloric acid, potassium dihydrogencitrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid or sodium chloride/glycine/hydrochloric acid.

4. The 2-part hair dyeing agent according to claim 1, wherein at least one of said first agent and said second agent contains a hair conditioning agent.

5. A 2-part hair dyeing agent which comprises:
a first agent comprising about 0.1 to 30% by weight of at least one compound capable of forming $HCO_3-$ by dissociation in water and about 0.001 to 10% by weight of a hair dye, wherein the weight percentages are based on the total weight of the first agent, and an alkali which generates substantially no irritating odor selected from the group consisting of an alkali metal hydroxide, an alkali earth metal hydroxide, lysine, oxylysine, histidine and aminoalkylpropanediol and in an amount such that the pH of the first agent is in the range of from 8.2 to 9.0, and
a second agent comprising about 0.1 to 6% by weight based on the total weight of the second agent of hydrogen peroxide and a buffer solution in an amount such that the pH of the second agent is in the range of from 2.0 to 4,0,
wherein the weight ratio of the first agent to the second agent when mixed, is characterized in that the resulting pH of the mixture is within a range of from 6.5 to 7.9.

* * * * *